United States Patent [19]

Suzuki et al.

[11] Patent Number: 4,929,267
[45] Date of Patent: May 29, 1990

[54] PLANT GROWTH PROMOTION

[75] Inventors: Akinori Suzuki, Chiba; Suong B. Hyeon, Urawa; Toshio Kajita, Yachiyo; Masakazu Furushima, Nagareyama; Shigeo Yoshinaka, Niigata; Takashi Suzuki, Niigata; Mitsunori Oda, Niigata; Akinori Tanaka, Niigata, all of Japan

[73] Assignee: Mitsubishi Gas Chemical Company, Japan

[21] Appl. No.: 938,872

[22] Filed: Dec. 8, 1986

[51] Int. Cl.$^5$ .............................. A01N 33/08
[52] U.S. Cl. ........................... 71/77; 71/106; 71/107; 71/111; 71/121
[58] Field of Search .................. 71/121, 77, 106, 107, 71/111; 260/501.15

[56] References Cited

U.S. PATENT DOCUMENTS

| | | | |
|---|---|---|---|
| 3,416,913 | 12/1968 | Zeisig et al. | 71/92 |
| 3,671,219 | 6/1972 | Nickell | 71/121 |
| 4,309,205 | 1/1982 | Kessler | 71/121 |
| 4,311,517 | 1/1982 | Youngman et al. | 71/121 |
| 4,488,901 | 12/1984 | Farkas et al. | 71/121 |
| 4,701,211 | 10/1987 | Dunbar et al. | 71/121 |

FOREIGN PATENT DOCUMENTS

| | | | |
|---|---|---|---|
| 1441422 | 9/1964 | France . | |
| 46-6804 | 2/1971 | Japan | 71/111 |

OTHER PUBLICATIONS

Chem. Abst., vol. 67, 2355b, Toyo Koatsu Industries, 1965, "Choline Derivatives as Plant Growth Regulators".

Takagi et al., "The Effects of Choline and its Analogs, etc.", C. A., vol. 66, 114267k, 1967, pg. 10,606.

Primary Examiner—Glennon H. Hollrah
Assistant Examiner—Susan P. Treanor

[57] ABSTRACT

Use of agriculturally acceptable salts of compounds of the following formula for promoting the growth of plants.

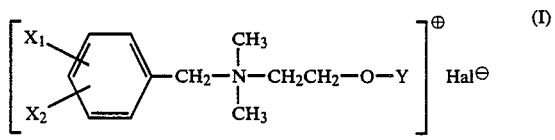

wherein Hal represents a chlorine, bromine or iodine atom, $X_1$ represents a hydrogen or chlorine atom, or a methyl, trifluoromethyl, nitro, methoxy or t-butyl group, and $X_2$ represents a hydrogen atom, or both $X_1$ and $X_2$ represent a chlorine atom or a methyl group; and Y represents a hydrogen atom, or a $C_{2-6}$ alkylcarbonyl, benzoyl, N-phenylcarbamoyl, N-3,4-dichlorophenylcarbamoyl, chloropropylcarbonyl, methoxycarbonyl, carbamoyl or methacryloyl group.

6 Claims, No Drawings

PLANT GROWTH PROMOTION

This invention relates to the promotion of plant growth, and more specifically, to a method of promoting the photosynthetic action and root-forming action of a plant and promoting its growth.

One method of increasing the ability of a plant to produce a substance is to increase its photosynthetic ability. Some attempts have been made to promote the photosynthesis of plants by selecting substrates or employing chemical means. For example, choline salts are known to have a plant growth promoting effect. U.S. Pat. No. 4,309,205 discloses a method of increasing the quantity and quality of flowers and fruits of a plant growing in soil which comprises applying to a mature plant during its reproductive stage a flower or fruit quantity and quality improving effective amount of at least one non-toxic salt of choline in an aqueous medium. U.S. Pat. No. 4,488,901 discloses a method of increasing the cold resistance of a plant, which comprises treating a cultivated plant before a temperature drop with an aqueous solution of at least one compound of the formula $HO\text{-}(CH_2)_n\text{-}NH_2$ wherein n is an integer of 2 to 5 or its N,N,N-trimethyl-quaternary ammonium salt thereof.

The present inventors have long worked in search of a substance capable of effectively promoting the photosynthetic and root-forming action of plants by chemical treatment, and have now found that a certain aminoethanol derivative has a cytokinin action and the ability to promote significantly the photosynthetic, growing and root-forming actions of plants.

According to this invention, there is provided a method of promoting the growth of a plant, which comprises applying an effective amount of at least one active compound selected from the group consisting of agriculturally acceptable salts of compounds represented by the formula

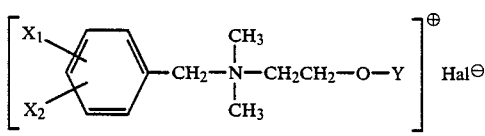

wherein Hal represents a chlorine, bromine or iodine atom, $X_1$ represents a hydrogen or chlorine atom, or a methyl, trifluoromethyl, nitro, methoxy or t-butyl group, and $X_2$ represents a hydrogen atom, or both $X_1$ and $X_2$ represent a chlorine atom or a methyl group; and Y represents a hydrogen atom, or a $C_{2-6}$ alkylcarbonyl, benzoyl, N-phenylcarbamoyl, N-3,4-dichlorophenylcarbamoyl, chloropropylcarbonyl, methoxycarbonyl, carbamoyl or methacryloyl group, to the stalks, leaves, roots or seeds of the plant or to soil.

In formula (I), the alkyl moiety of the $C_{2-6}$ alkylcarbonyl group represented by Y may be linear or branched, and specific examples of the $C_{2-6}$ alkylcarbonyl group include acetyl, propionyl, n-butyryl, isobutyryl, n-valeryl, caproyl and capryloyl groups.

In formula (I), the moiety

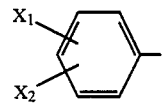

is preferably one in which both $X_1$ and $X_2$ are hydrogen atoms, or one in which $X_1$ is a 2-methyl or 3-methyl group, and $X_2$ is a hydrogen atom.

The agriculturally acceptable salts of the compounds of formula (I) include, for example, hydrohalogenates such as hydrochlorides and hydrobromides, inorganic acid salts such as phosphates, nitrates, sulfates and carbonates, and organic acid salts such as acetates, citrates, lactates and L(+)-tartrates. Of these, the hydrochlorides and hydrobromides are preferred.

The agriculturally acceptable salt of the compounds of formula (I) can be produced, for example, by (a) reacting an N,N-dimethyl ethanolamine compound represented by the formula

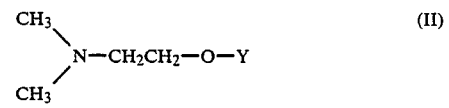

wherein Y is as defined hereinabove, with a halide represented by the formula

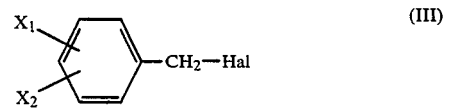

wherein Hal represents a halogen atom, and $X_1$ and $X_2$ are as defined above,
to obtain a compound represented by the following formula

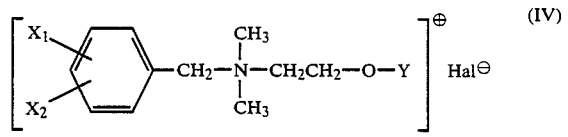

wherein $X_1$ and $X_2$ are as defined above, or
(b) reacting a compound of formula (IV) in which Y is a hydrogen atom with a $C_{2-6}$ alkylcarbonyl halide, $C_{2-6}$ alkanoic acid anhydride, benzoyl halide, N-phenylcarbamoyl halide, N-3,4-dichlorophenylcarbamoyl halide, chloropropylcarbonyl halide or methoxycarbonyl halide, carbamoyl halide or methacryloyl halide to form a compound of formula (I) wherein Y is as defined but other than a hydrogen atom.

Some embodiments of their production are shown below.

PRODUCTION EXAMPLE 1

Under ice cooling, 4.83 g (30 millimoles) of 2-chlorobenzyl chloride was added to 2.67 g (30 millimoles) of dimethylethanolamine dissolved in 10 ml of ether. The mixture was left to stand at room temperature for 2 days. The crystals that precipitated were separated by filtration, washed with ether, and dried under reduced pressure to give N-2-chlorobenzyl-N,N-dimethyl-2-hydroxyethanol ammonium chloride (compound No. 4 in Table 1 given hereinbelow) represented by the following formula.

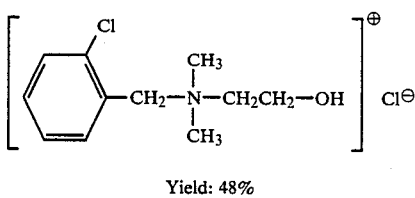

Yield: 48%

PRODUCTION EXAMPLE 2

In 20 ml of isopropyl ether were dissolved 4.47 g (30 millimoles) of 2-dimethylaminoethyl butyrate

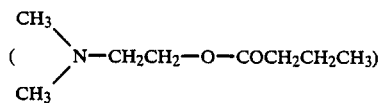

and 3.8 g (30 millimoles) of benzyl chloride, and the solution was left to stand at room temperature for 4 days. The solvent was then evaporated. The crystals that precipitated were separated by suction filtration, washed fully with isopropyl ether, and dried under reduced pressure to give N-benzyl-N-(2-butyryloxyethyl)-N,N-dimethylammonium chloride (compound No. 29 in Table 1 given hereinbelow) represented by the following formula.

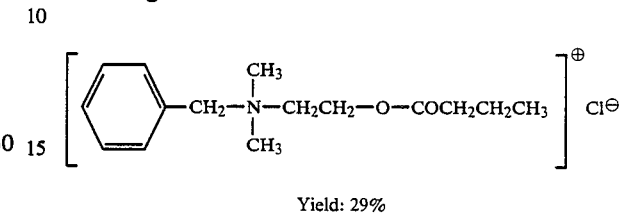

Yield: 29%

In the same way as in Production Examples 1 and 2, the salts of compounds of formula (I) shown in Table 1 can be obtained. Table 1 also describes the compounds obtained in Production Examples 1 and 2.

TABLE 1

| Compound No. | $X_1$ | $X_2$ | Y | Salt | m.p. (°C.) | IR spectrum ($\nu cm^{-1}$) | NMR spectrum ($\Delta ppm$) |
|---|---|---|---|---|---|---|---|
| 1 | 2-$CH_3$ | H | H | Cl | 71–74 | 3290, 1462, 1070, 845, 776, 745 | 2.47(s, 3H) 3.12(s, 6H) 3.63(t, J = 5 Hz, 2H) 4.17(m, 2H) 4.62(s, 2H) 7.46(bs, 4H) |
| 2 | 3-$CH_3$ | H | H | I | 76–78 | 3250, 1450, 1072, 974, 806 | — |
| 3 | 4-$CH_3$ | H | H | Cl | — | 3250, 1450, 1072, 974, 806 | 2.42(s, 3H) 3.12(s, 6H) 3.55(t, J = 5 Hz, 2H) 4.15(m, 2H) 4.55(s, 2H) 7.42(s, 4H) |
| 4 | 2-Cl | H | H | Cl | — | 3275, 1470, 1446, 1082, 1052, 766 | 3.20(s, 6H) 3.70(t, J = 5 Hz, 2H) 4.22(m, 2H) 4.77(s, 2H) 7.63(m, 4H) |
| 5 | 3-Cl | H | H | Cl | — | 3215, 1468, 1080, 856, 838 | — |
| 6 | 3-Cl | H | H | I | 111–114 | 3280, 1053, 909, 874, 775, 698 | 3.14(s, 6H) 3.50(t, J = 5 Hz, 2H) 4.14(m, 2H) 4.59(s, 2H) 7.4–7.7(m, 4H) |
| 7 | 4-Cl | H | H | Cl | 118–120 | 3215, 1468, 1080, 856, 838 | 3.17(s, 6H) 3.58(t, J = 6 Hz, 2H) 4.17(m, 2H) 4.63(s, 2H) 7.60(s, 4H) |
| 8 | 4-$NO_2$ | H | H | Br | 121–124 | 3290, 1518, 1346, 1068, 904, 842 | DMSO $d_6$ 3.15(s, 6H) 3.54(T, J = 5 Hz, 6H) 4.12(m, 2H) 4.72(s, 2H) 7.85(d, J = 8 Hz, 2H) 8.38(d, J = 8 Hz, 2H) |
| 9 | 4-$CF_3$ | H | H | Br | 102–104 | 3210, 1320, 1112, 1062, 860, 846 | 3.30(s, 6H) 3.71(t, J = 5 Hz, 2H) 4.31(m, 2H) 4.84(s, 2H) 7.93(s, 4H) |
| 10 | 2-Cl | 4-Cl | H | Cl | 126–128 | 3240, 1464, 1070, 900, 812 | 3.17(s, 6H) 3.66(t, J = 5 Hz, 2H) 4.15(m, 2H) 4.75(s, 2H) 7.51 (d, J = 8 Hz, 1H) 7.64(d, J = 8 Hz, 1H) 7.70(s, 1H) |
| 11 | 2-Cl | 6-Cl | H | Br | 144–145 | 3230, 1421, 1082, 960, 787, 749 | 3.24(s, 6H) 3.76(t, J = 5 Hz, 2H) 4.19(m, 2H) 4.99(s, 2H) 7.59(bs, 3H) |
| 12 | 2-Cl | 5-Cl | H | Cl | 137–139 | 3130, 1474, 1115, 807 | 2.37(s, 3H) 2.41(s, 3H) 3.11 (m, 6H) 3.61(t, J = 5 Hz, 2H) 4.15 (m, 2H) 4.57(s, 2H) 7.32 (s, 5H) |
| 13 | 3-$CF_3$ | H | H | Br | — | 3210, 1320, 1112, 1062, 860, 846 | |
| 14 | 3-$CF_3$ | 4-$CH_3$ | H | Br | 113–116 | 3240, 1441, 1091, 812 | 2.32(s, 6H) 3.09(s, 6H) 3.50(t, J = 5 Hz, 2H) 4.13(m, 2H) 4.69(s, 2H) 7.32(bs, 3H) |
| 15 | H | H | $COCH_3$ | Br | 127–130 | 1724, 1220, 1050, 914, 764, 712 | 2.18(s, 3H) 3.15(s, 6H) 3.75(t, J = 5 Hz, 2H) 4.61(bs, 4H) 7.60(s, 5H) |
| 16 | H | H | $COCH(CH_3)_2$ | Cl | 127–128 | 1728, 1144, 769, 717 | 1.21(d, J = 7 Hz, 6H) 2.77(hep, J = 7 Hz, 1H) 3.17(s, 6H) 3.76(t, J = 5 Hz, 2H) 4.64(bs, 4H) 7.63(s, 5H) |
| 17 | H | H | $COCH_2CH_2CH_2Cl$ | Br | 99–101 | 1735, 1155, 785, 766, 713 | 2.13(q, J = 6.5 Hz, 2H) 2.67(t, J = 6.5 Hz, 2H) 3.17(s, 6H) 3.70 |

TABLE 1-continued

| Compound No. | $X_1$ | $X_2$ | Y | Salt | m.p. (°C.) | IR spectrum ($\nu cm^{-1}$) | NMR spectrum ($\Delta$ppm) |
|---|---|---|---|---|---|---|---|
| 18 | H | H | $CO(CH_2)_4CH_3$ | Cl | 80–82 | 1726, 1154, 761, 707 | (t, J = 6.5 Hz, 2H) 3.77(t, J = 5 Hz, 2H) 4.64 (bs, 4H) 7.62(s, 5H) |
| 19 | H | H | $CO(CH_2)_4CH_3$ | Br | 111–112 | 1726, 1154, 762, 709 | 0.93(t-like, J = 6.5 Hz, 3H) 1.15–1.50(m, 4H) 1.62(m, 2H) 2.53(t, J = 6.5 Hz, 2H) 3.25(s, 6H) 3.84(t, J = 5 Hz, 2H) 4.72(bs, 4H) 7.69(s, 5H) |
| 20 | H | H | $CO-C_6H_5$ | Cl | 167–170 | 1718, 1262, 1117, 764, 702 | 3.25(s, 3H) 3.96(m, 2H) 4.70(s, 2H) 4.88(m, 2H) 7.55–7.88(m, 8H) 8.07(dd, J = 10, 1 Hz, 2H) |
| 21 | H | H | $COOCH_3$ | Br | 147–148 | 1743, 1434, 1264, 920, 781, 766, 713, 700 | |
| 22 | H | H | $CONHC_6H_5$ | Br | 161–162 | 3190, 1724, 1590, 1432, 1205, 743, 702, 685 | 3.15(s, 6H) 3.78(t, J = 5 Hz, 2H) 4.69(t-like, 2H), 4.76(s, 2H) 7.0–7.9(m, 10H) |
| 23 | H | H | $CONH(4-Cl)C_6H_4$ | Br | 184–186 | 3180, 3150, 1729, 1524, 1203, 1073, 998, 703 | 3.16(s, 6H) 3.79(t, J = 5 Hz, 2H) 4.69(m, 2H) 4.78(s, 2H) 7.40 (d, J = 9 Hz, 2H) 7.58(d, J = 9 Hz, 2H) 7.61(s, 5H) |
| 24 | H | H | $CONH(3,4DiCl)C_6H_3$ | Br | 203–205 | 3190, 1729, 1583, 1202, 1066, 695 | 3.22(s, 6H) 3.79(m, 2H) 4.75(bs, 4H) 7.61(bs, 7H) 7.85(s, 1H) |
| 25 | H | H | $COC(CH_3)=CH_2$ | Cl | 108–110 | 1717, 1288, 1158, 1148, 764, 717 | 1.98(s, 3H) 3.19(s, 6H) 3.84(t, J = 5 Hz, 2H) 4.65(s, 2H) 4.76(m, 2H) 5.82(bs, 1H) 6.20(bs, 1H) 7.63(bs, 5H) |
| 26 | H | H | $CONH_2$ | Br | 124–126 | 3300, 1715, 1322, 1098, 758, 704 | 3.12(s, 6H) 3.70(t, J = 5 Hz, 2H) 4.56(m, 2H) 4.59(s, 2H) 7.58(s, 5H) |
| 27 | H | H | $COCH_2CH_3$ | Cl | — | 1729, 1216, 1078, 995, 762, 708 | 1.14(t, J = 7.5 Hz, 3H) 2.50 (q, J = 7.5 Hz, 2H) 3.15(s, 6H) 3.75(t, J = 5 Hz, 2H) 4.61(bs, 4H) 7.61(s, 5H) |
| 28 | H | H | $CO(CH_2)_2CH_3$ | Br | — | 1726, 1170, 756, 704 | — |
| 29 | H | H | $CO(CH_2)_2CH_3$ | Cl | — | 1734, 1154, 760, 710 | 0.95(t, J = 7.5 Hz, 3H) 1.66(hex, J = 7.5 Hz, 2H) 2.47(t, J = 7.5 Hz, 2H) 3.16(s, 6H) 3.81(t, J = 5 Hz, 2H) 4.62(bs, 4H) 7.62(s, 5H) |
| 30 | 3-Cl | H | $COOCH_3$ | Cl | — | 1749, 1469, 1433, 1262, 923, 781 | 3.18(s, 6H) 3.77(m, 2H) 3.89(s, 3H) 4.70(m, 2H) 7.62(m, 3H) |
| 31 | 2-Cl | H | $COC_6H_5$ | Cl | 157–158 | 1722, 1265, 1108 708 | 3.28(s, 6H) 3.96(t, J = 5 Hz, 2H) 4.70(s, 2H) 4.90(m, 2H) 7.5–7.9 (m, 7H) 8.08(d, J = 7 Hz, 2H) |
| 32 | 3-Cl | H | $COC_6H_5$ | Cl | 144–145 | 1716, 1264, 1114, 700 | 3.29(s, 6H) 4.04(t, J = 5 Hz, 2H) 4.86(s, 2H) 4.94(m, 2H) 7.4–7.9(m, 7H) 8.07(d, J = 7 Hz, 2H) |
| 33 | 3-Cl | H | $COC_6H_5$ | Cl | 189–190 | 1712, 1271, 1115, 707 | 3.26(s, 6H) 3.94(t, J = 5 Hz, 2H) 4.70(s, 2H) 4.92(m, 2H) 7.61(m, 7H) 8.07(d, J = 7 Hz, 2H) |
| 34 | 2-$CH_3$ | H | $COC_6H_5$ | Cl | 152–153 | 1720, 1262, 1107, 704 | 2.55(s, 3H) 3.27(s, 6H) 4.05(m, 2H) 4.75(s, 2H) 4.93(m, 2H) 7.4–7.9(m, 7H) 8.08(d, J = 8 Hz, 2H) |
| 35 | 3-$CH_3$ | H | $COC_6H_5$ | Cl | 125–128 | 1718, 1267, 1112, 708 | 2.46(s, 3H) 3.25(s, 6H) 3.92(t, J = 5 Hz, 2H) 4.60(s, 2H) 4.91(m, 2H) 7.4–7.8(m, 7H) 8.03(d, J = 7 Hz, 2H) |
| 36 | 4-$CH_3$ | H | $COC_6H_5$ | Cl | 162–164 | 1718, 1266, 1105, 705 | 2.43(s, 3H) 3.20(s, 6H) 3.91(t, J = 5 Hz, 2H) 4.63(s, 2H) 4.86(m, 2H) 7.4–7.8(m, 7H) 8.06(d, J = 7 Hz, 2H) |
| 37 | 4-$NO_2$ | H | $COC_6H_5$ | Br | 187–188 | 1717, 1265, 1115, 704 | (buso-db) 3.16(s, 6H) 3.90(m, 2H) 4.64(s, 2H) 4.83(m, 2H) 7.59(m, 7H) 8.07(d, 7 Hz, 2H) |
| 38 | 2-Cl | 6-Cl | $CO(CH_2)_2CH_3$ | Br | 110–113 | 1734, 1425, 1152, 776, 753 | 0.94(t, J = 7 Hz, 3H) 1.66(hex, J = 7 Hz, 2H) 2.47(t, J = 7 Hz, 2H) 3.28(s, 6H) 4.01(t, J = 5 Hz, 2H) 4.73(m, 2H) 5.01(s, 2H) 7.61(bs, 3H) |
| 39 | 2-$CH_3$ | 5-$CH_3$ | $CO(CH_2)_2CH_3$ | Cl | 157–158 | 1730, 1473, 1169, 806 | 0.92(t, J = 7 Hz, 3H) 1.64(hex, J = 7 Hz, 2H) 2.37(s, 3H) 2.42(s, 3H) 2.44(s, J = 7 Hz, 2H) 3.12(s, 6H) 3.80(t, J = 5 Hz, 2H) 4.61(bs, |

TABLE 1-continued

| Compound No. | $X_1$ | $X_2$ | Y | Salt | m.p. (°C.) | IR spectrum ($\nu cm^{-1}$) | NMR spectrum ($\Delta$ppm) |
|---|---|---|---|---|---|---|---|
| 40 | 4-NO$_2$ | H | CO(CH$_2$)$_2$CH$_3$ | Br | 55–57 | 1732, 1513, 1340, 1165, 836 | 4H) 7.33(bs, 3H) (D$_2$O-DMSO) 0.85(t-like, 2H) 1.1–1.9(m, 6H) 2.43(t, J = 7 Hz, 2H) 3.13(s, 6H) 3.79(m, 2H) 4.56(m, 2H) 4.7(s, 2H) 7.84(d, J = 9 Hz, 2H) 8.38(d, J = 9 Hz, 2H) |
| 41 | 2-CH$_3$ | 5-CH$_3$ | CO(CH$_2$)$_4$CH$_3$ | Cl | 144–145 | 2940, 1736, 1476, 1166, 808 | 0.85(t-like, 3H) 1.05–1.9(m, 6H) 2.2–2.6(m, 8H) 3,12(s, 6H) 3.84(m, 2H) 4.65(m, 4H) 7.33(m, 3H) |
| 42 | 4-NO$_2$ | H | CO(CH$_2$)$_4$CH$_3$ | Br | 156–157 | 2930, 1745, 1515, 1344, 1163, 847 | 0.93(t, J = 7 Hz, 3H) 1.65(hex, J = 7 Ht, 2H) 2.47(t, J = 7 Hz, 2H) 3.21(s, 6H) 3.83(t, J = 5 Hz, 2H) 4.64(m, 2H) 4.77(s, 2H) 7.85(d, J = 10 Hz, 2H) 8.39(d, J = 10 Hz, 2H) |
| 43 | H | H | H | Cl | 72–74 | 3300, 1475, 1088, 772, 728 | 3.11(s, 6H) 3.53(t, J = 5 Hz, 2H) 3.59(m, 2H) 4.12(s, 2H) 7.59(s, 5H) |
| 44 | H | H | H | Br | 124–126 | — | |
| 45 | H | H | H | I | 145–147 | — | |
| 46 | 4-Cl | H | COOCH$_3$ | Cl | 120–121 | 1760, 1488, 1445, 1272 | — |
| 47 | 4-Cl | H | CO(CH$_2$)$_2$CH$_3$ | Cl | hydroscopic | 1732, 1476, 1152, 1078 | — |
| 48 | 4-C(CH$_3$)$_3$ | H | H | Br | 119–122 | 3220, 2960, 1474, 1355, 1094, 838 | — |
| 49 | 2-Cl | —4Cl | CO(CH$_2$)$_4$CH$_3$ | Cl | 92–94 | 1740, 1464, 1163, 1148, 818 | — |
| 50 | 4-CH$_3$O | H | H | Cl | 109–111 | 3310, 1608, 1508, 1252, 1180, 1023 | — |

Among these compounds, compounds Nos. 1, 2, 3, 9, 12, 13, 15, 16, 18, 19, 21, 26, 27, 28, 29, 43, 44 and 45 are preferred. Compounds Nos. 1, 2, 15, 27, 28 and 29 are particularly preferred because they are effective at low dosages. Compounds Nos. 15, 18, 21, 26, 27, 28, 29 and 43 have high cytokinin activity. Compounds Nos. 1, 2, 3, 4, 6, 12, 13, 15, 29 and 43 have high growth promoting activity and high root-formation promoting activity.

The agriculturally acceptable salts of the compounds of formula (I) (to be generically referred to as the active compound of the invention) have the ability to increase the photosynthetic action and/or root-forming action of plants and to promote the growth of the plants. There is no particular limitation on the plants whose growth can be promoted in accordance with this invention, and they may include various agriculturally or horticulturally cultivated plants. Specific examples include cereal plants such as rice, wheat, barley, and corn, leguminous plants such as soybean and adzuki bean; plants having underground tubers or bulbs such as onion, garlic and potato; vegetables grown for their edible roots such as radish, sweet potato, beet and carrot; fruits such as peach, persimmon, grape and apple; vegetables grown for their edible fruits such as tomato and cucumber; vegetables grown for their edible leaves such as lettuce, cabbage, cauliflower and spinach; and flowers such as tulip and cosmos.

The active compound of this invention may be formulated for application in any known form, such as a wettable powder, granules, an aqueous solution, an emulsifiable concentrate or an aqueous suspension, using a conventional agriculturally acceptable carrier or diluent. There is no special restriction on the carrier or diluent used in the formulation so long as they are agriculturally acceptable. For example, talc, clay and bentonite may be used as a carrier for a wettable powders and granules. The aqueous solution is most preferred as the form in which the active compound is applied.

The resulting formulations may contain the active compound of the invention in an amount of 1 to 75% by weight, preferably 30 to 75% by weight. Such formulations may further contain another conventional agriculturally active ingredient such as a fertilizer, herbicide, insecticide or bactericide.

The formulations may desirably contain a surfactant. The amount of the surfactant is, for example, 0.02 to 20% by weight, preferably 0.1 to 5% by weight, depending upon the form of the formulation to promote the adsorption and penetration of the active ingredients. Preferred surfactants may include nonionic surfactants such as polyoxyethylene alkyl ethers (e.g. polyoxyethylene lauryl ether), and anionic surfactants such as lauryl sulfonate triethanolamine salt.

The active compound of this invention may be applied by any methods known per se. For example, it may be sprayed onto the stalks and leaves of mature plants, or poured onto parts near the roots. Seeds are preferably immersed in a solution containing the active compound of the present invention.

The rate of application of the active compound of the invention varies, for example, with the type of a plant to be treated, the stage of plant growth, and the manner and timing of application. For example, for spraying onto the stalks and leaves of a plant, the rate of application of the active compound of the invention normally ranges from 3 to 1,500 g, preferably from 10 to 1,000 g, per hectare of the cultivated area. An aqueous solution is a preferred type of formulation for foliar application, and may contain the active compound of the invention in a concentration of 10 to 100,000 ppm, particularly 20 to 50,000 ppm.

Generally, the good time of applying the active compound of the invention is when photorespiration of the plant is at its peak. For example, it is desirably applied at some point during a period from the reproductive growth to the harvesting time. To some plants, however, application during vegetative growth may provide more desirable effects. In other words, there is no specific limit to the timing of application.

In the case of pouring the active compound of the invention, it is usually advantageous to apply an aqueous solution containing the active compound of the invention in a concentration of 0.1 to 300 ppm, preferably 0.5 to 100 ppm, to parts near the roots of a plant at a rate of 5 to 100 m$^3$, preferably 10 to 50 m$^3$, per hectare.

When the active compound of this invention is used to treat plant seeds, it is suitable to immerse the seeds in an aqueous solution normally containing 0.05 to 1,000 ppm, preferably 0.1 to 300 ppm, for about 1 to about 48 hours, preferably about 3 to about 24 hours.

To use the active compound of the invention for root formation or anchoring of rice seedlings, it is the general practice to pour an aqueous solution of the active compound onto the roots of the rice seedlings before transplantation.

The method, time and rate of application and the expected effect of the active compound of the invention on typical plants are summarized in Table 2.

For example, the active compound of this invention can promote the root formation of $C_3$ plants such as rice, wheat, barley, beet, sweet potato, potato and onion and $C_4$ plants such as corn and sugarcane, nurse their sound seedlings, promote their growth in the early stage, and increase the harvest of the crops. Furthermore, it can increase the sweetness and size of fruits such as apple, persimmon, peach, orange and lemon, promote their coloration, and maintain their freshness. It can further promote size increase of bulbs of flowers such as tulip, and promote the flowering of cosmos, etc.

For application of the active compound of the invention to plants, it may be formulated into a wettable powder, an aqueous solution, a suspension in water or oil, etc. Typical formulation examples are given below.

FORMULATION EXAMPLE 1

Aqueous solution

Fifty grams of compound No. 15, 10 g of polyoxyethylene oleyl ether and 10 g of triethanolamine lauryl sulfate and 180 g of pure water are mixed to prepare an aqueous solution containing 20% of compound No. 15. Usually, it is used after it is diluted to 100 to 2000 times.

FORMULATION EXAMPLE 2

Wettable powder

TABLE 2

| Crop | Method of application | Time of application | Rate of application | Expected effect |
|---|---|---|---|---|
| rice, wheat, barley | foliar | from 40 days before heading to 10 days after heading | 50–1000 g/ha | increased harvest |
| soybean (leguminous plants) | foliar | from 10 days before flowering to 20 days after flowering | 20–300 g/ha | increased harvest (increased number of pods) |
| onion, garlic tulip | foliar | early stage of bulb swelling | 20–300 g/ha | bulb swelling |
| potato | foliar | early stage of tuber growth | 20–300 g/ha | tuber growth and increased yield |
| peach, persimmon, grape, apple | foliar | flowering stage to 10 days before harvest | 3–300 g/ha | size increase of fruits, increase of sweetness, maintenance of freshness |
| wheat, barley | foliar | 2- to 3-leaf stage | 3–300 g/ha | growth promotion |
| rice | seed treatment | immersed for 24 hours after immersion in water for 2 days | 0.1–300 ppm | promotion of growth and root formation |
| wheat, barley | seed treatment | immersed for 24 hours | 0.1–300 ppm | promotion of growth and root formation |
| tomato, lettuce | seed treatment | immersed for 24 hours | 0.1–300 ppm | promotion of growth and root formation |
| rice seedling | pouring | from the 2-leaf stage to the time before transplantation | 0.5–50/ mg 1800 cm$^2$ (1–100 ppm) | promotion of growth and root formation |
| tomato seedling | pouring | seedling stage | 0.1–10 mg seedling (1–100 ppm) | growth promotion |

By applying the agriculturally acceptable salt of the compound of formula (I) to a plant in accordance with this invention, the photosynthetic action and root-forming action of the plant can be greatly increased, and consequently, the growth of the plant can be promoted.

Fifty grams of compound No. 29, 2 g of sodium dodecylbenzenesulfonate, 1 g of polyoxyethylene alkyl aryl ether, 10 g of talc, and 37 g of bentonite are uniformly mixed and pulverized to give a wettable powder containing 50% of compound No. 29.

The excellent plant growth promoting activity of the active compounds of this invention are demonstrated by the following Test Examples.

TEST EXAMPLE 1

Photosynthesis using protoplasts

Wheat (Variety: Norin No. 61) was cultivated for 10 days in vermiculite as soil in a phytotron kept at 25° C. in the day time under natural light and 20° C. at night. Protoplasts were isolated from the wheat by a conventional method [see Plant Physiol. (1978), 62, 313-319]. The effect of the protoplasts on photosynthesis was examined in the following manner using an oxygen electrode.

The protoplasts were incubated for 1 minute with the test compound in a reaction solution [50 mM HEPES-KOH buffer (pH 7.6), 0.4M sorbitol, 1 mM EDTA, 10 mM sodium hydrogen carbonate], and then light (100,000 lux) was irradiated to initiate photosynthesis. The activity was examined in comparison with a non-treated lot (containing no test compound). The results are shown in Table 3.

TABLE 3

| Compound No. | Concentration (mM) | Increase in photosynthesis (*) |
|---|---|---|
| 1 | 10 | +++ |
| 3 | " | ++ |
| 4 | " | ++++ |
| 5 | " | +++ |
| 7 | " | ++ |
| 9 | " | +++ |
| 13 | " | ++++ |
| 16 | " | +++ |
| 18 | " | +++ |
| 20 | " | ++ |
| 23 | " | ++ |
| 26 | " | +++ |
| 27 | " | +++ |
| 29 | " | +++ |
| 35 | " | ++ |
| 39 | " | ++ |
| 41 | " | ++ |
| 42 | " | ++ |
| 43 | " | +++ |

(*) −: Decreased from that in the non-treated lot.
±: Same as non-treated lot.
+: 0-5% increase from non-treated lot.
++: 5-10% increase from non-treated lot.
+++: 10-15% increase from non-treated lot.
++++: More than 15% increase from non-treated lot.

TEST EXAMPLE 2

Cytokinin activity was examined by using cucumber in accordance with the method of R. A. Fletcher and D. McCullagh [Planita, 101, 88 (1971)].

Seeds of cucumber (a green ground crawling species with long nodes) were immersed in water for 3 to 4 hours, and then sown in fully watered nursing boxes (30×20×3 cm) containing vermiculite at a rate of 200 per box. The seeds were nursed for 5 days at 28° C. in the dark, and the emerged yellow cotyledons were cut off under pale green light. Twenty pairs of the cotyledons were put in a Petri dish having a diameter of 9 cm containing 5 ml of 2 mM phosphate buffer (pH 6.0) containing each of the test compounds shown in Table 4 in a concentration of 10 ppm. The Petri dish was maintained in the dark at 28° C. for 15 hours, and then placed under day light fluorescent lamp (3000 to 4000 luxes) for 4 hours. Five pairs of the cotyledons which turned green were extracted with acetone, and the amount of chlorophyl per unit weight of the raw cotyledons was calculated. The results are shown in Table 4.

TABLE 4

| Compound No. | Concentration (ppm) | Weight ratio of the cotyledons to the non-treated area (*) | Amount of chlorophyl (the ratio to the non-treated area) (*) |
|---|---|---|---|
| Non-treated | — | 100 (205 mg/5) | 100 (70.8 kg/g) |
| 15 | 10 | 107 | 199 |
| 21 | 10 | 106 | 186 |
| 18 | 10 | 105 | 182 |
| 26 | 10 | 101 | 179 |
| 28 | 10 | 103 | 177 |
| 13 | 10 | 105 | 165 |
| 27 | 10 | 106 | 204 |
| 29 | 10 | 99 | 199 |
| 43 | 10 | 105 | 185 |

(*): Relative proportion when the value in the non-treated area is taken as 100.

The active compounds in accordance with this invention show a high effect in an actual field test in spite of having nearly the same cytokinin activity as benzyladenine. This is considered to be because the active compounds of this invention are well absorbed and transferred to the plant body. Another cause would be that the cytokinin activity of the active compounds of this invention is suitable for the growth promotion of the plants. The active compounds of this invention have the advantage of being much better soluble in water than zeatin and benzyladenine.

The foregoing is considered to be the reason why the active compounds show a higher effect in a field test than in a basic indoor test.

TEST EXAMPLE 3

Upland farm soil was put in Wagner pots (1/5000 a) and a chemical fertilizer (N: 0.2 g, P: 0.48 g, K: 0.32 g) was applied as a base fertilizer at a rate of 2 g/pot.

On March 5, soybean (variety: Okuhara HS-1) which had been immersed for 20 hours in each of the test chemicals in each of the concentrations shown and washed with water were sown at a rate of one per pot, and grown in a greenhouse. In the non-treated area, the soybean was immersed in water for 20 hours. On March 15, 10 days after the sowing, the seedlings were reaped, and the dry weights of the stalks and leaves and the underground portion were measured.

The results are shown in Table 5.

TABLE 5

| Compound No. | Concentration (ppm) | Ratio to the non-treated area | |
|---|---|---|---|
| | | Dry weight of the stalks and leaves | Dry weight of the root portion |
| Non-treated | — | 100 (1.0 g/plant) | 100 (0.3 g/plant) |
| 1 | 100 | 158 | 217 |
| | 10 | 148 | 213 |
| 2 | 100 | 160 | 210 |
| | 10 | 168 | 243 |
| 3 | 100 | 160 | 190 |
| | 10 | 168 | 133 |
| 13 | 100 | 123 | 143 |
| | 10 | 158 | 217 |
| 15 | 100 | 166 | 227 |
| | 10 | 146 | 193 |
| 29 | 100 | 149 | 210 |

TABLE 5-continued

| Compound No. | Concentration (ppm) | Ratio to the non-treated area | |
|---|---|---|---|
| | | Dry weight of the stalks and leaves | Dry weight of the root portion |
| Non-treated | — | 100 (1.0 g/plant) | 100 (0.3 g/plant) |
| 12 | 10 | 157 | 205 |
| | 100 | 152 | 177 |
| 6 | 10 | 165 | 217 |
| | 100 | 160 | 233 |
| 4 | 10 | 150 | 183 |
| | 100 | 162 | 200 |
| 43 | 10 | 165 | 200 |
| | 100 | 158 | 195 |
| | 10 | 157 | 199 |

*Relative proportion when the value for the non-treated area is taken as 100.

TEST EXAMPLE 4

A liquid preparation containing each of the active compounds shown in Table 6 in a concentration of 50 ppm was sprayed onto clusters of grape (variety: Kyoho) three days before harvest until they were fully wet. After the lapse of days indicated in Table 6, the number of berries which dropped from the clusters after the harvest was measured. One area consisted of three clusters each of which had about 80 berries.

The resutls are shown in Table 6.

TABLE 6

| Compound No. | Cumulative total (%) | | | | |
|---|---|---|---|---|---|
| | 0 day | 5 days | 7 days | 9 days | 11 days |
| Non-treated | 0 | 6 | 15 | 26 | 41 |
| 3 | 0 | 0 | 0 | 15 | 24 |
| 13 | 0 | 0 | 0 | 4 | 17 |
| 15 | 0 | 0 | 0 | 5 | 18 |
| 26 | 0 | 0 | 0 | 7 | 14 |
| 29 | 0 | 0 | 0 | 3 | 11 |
| 43 | 0 | 0 | 0 | 10 | 16 |

TEST EXAMPLE 5

Paddy soil was filled in Wagner pots (1/5000 a), and a chemical fertilizer (nitrogen content 10%, phosphorus content 24%, potassium content 16%) was applied to the soil as a base fertilizer at a rate of 2 g/pot. On May 25, 6 rice seedlings (variety: "koshihikari") were transplanted in each pot, and cultivated in a green house. On July 18 (15 days before heading), an aqueous solution of each of the test compounds shown in Table 7 in the concentrations indicated (containing 200 ppm of polyoxyethylenealkyl aryl ether as a surfactant) was sprayed onto the leaves of the rice plants. One area consisted of four pots.

On September 20, the rice plants were reaped, and the amount of refined rice was examined. The results are shown in Table 7. In the non-treated area, only a mixture of the surfactant and water was used.

TABLE 7

| Compound No. | Dosage (g/10a) | Yield of refined rice (%, based on the yield the non-treated area) (*) |
|---|---|---|
| Non-treated | — | 100 (20.3 g/pot) |
| 1 | 10 | 126 |
| | 30 | 122 |
| 2 | 10 | 114 |
| | 30 | 125 |

TABLE 7-continued

| Compound No. | Dosage (g/10a) | Yield of refined rice (%, based on the yield the non-treated area) (*) |
|---|---|---|
| 15 | 10 | 134 |
| | 30 | 129 |

*Relative proportion when the yield of the non-treated area is taken as 100.

TEST EXAMPLE 6

Each of the test compounds in each of the dosages shown in Table 8 was dissolved in 100 liters of water, and 200 ppm of polyoxyethylene alkyl aryl ether was added as a surfactant. On May 10 (20 days before flowering), the solution was sprayed onto the leaves of wheat (variety: winter wheat "horoshiri"). On July 26, the wheat was harvested, and the dry weight of the overground portions (stalks and leaves) and the amount of harvest were measured.

In the non-treated area, only a mixture of water and the surfactant was sprayed.

The test results are shown in Table 8.

TABLE 8

| Compound No. | Dosage (g/10a) | Ratio to the non-treated area (*) | |
|---|---|---|---|
| | | Dry amount of the overground portions | Yield |
| Non-treated | — | 100 (1120 kg/10a) | 100 (541 kg/10a) |
| 1 | 20 | 111 | 116 |
| | 50 | 111 | 117 |
| 15 | 20 | 110 | 115 |
| | 50 | 112 | 118 |
| 27 | 20 | 113 | 120 |
| | 50 | 113 | 119 |

*Relative proportion when the weight or yield of the non-treated area is taken as 100.

TEST EXAMPLE 7

On June 28, soybean (variety: "enrei") and corn (dent corn) were sown in 1-liter plastic pots filled with volcanoic ash field soil, and germinated in a greenhouse at 25° C. Then, they were grown in a field. A base fertilizer was applied at a rate of 3 kg/10 a as nitrogen.

Polyoxyethylene alkyl aryl ether (100 ppm) as a spreader was added to a liquid preparation of each of the test chemicals indicated in Table 9 in a concentration of 300 ppm. The liquid preparation was sprayed by a sprayer onto soybean in the stage of developing 2 main leaves and to corn in the four-leaf stage so that the entire plants were fully wetted with the liquid preparation. A mixture of water and the spreader was applied to a non-treated area.

Every seven days after the treatment, the dry weight and the leaf area of 8 plant individuals were measured, and in accordance with the following Watson's equations, the relative growth rate (RGR) and the net assimiation rate (NAR) expressing the rate of increase in dry weight per unit area of the leaves of the individuals were calculated.

Calculating equations:

$$RGR = \frac{1}{w} \cdot \frac{dw}{dt} = \frac{\ln w_2 - \ln w_1}{t_2 - t_1}$$

-continued
$$NAR = \frac{1}{F} \cdot \frac{dw}{dt} = \frac{(w_2 - w_1) \cdot (\ln \bar{F}_2 - \ln \bar{F}_1)}{(t_2 - t_1) \cdot (\bar{F}_2 - \bar{F}_1)}$$

In these equations, $w_1$ represents the dry weight in the first measurement, and $w_2$ represents the dry weight in the next measurement; $t_2 - t_1$ is the day from the first measurement to the next measurement; and $(\bar{F}_1 - \bar{F}_2)$ represents an increase in the leaf area during that period.

The results are shown in Table 9.

It is seen from the test results that compounds Nos. 2 and 15 show higher RGR and NAR values than choline chloride.

TABLE 9

| Compound No. | Soybean | | Corn | |
| --- | --- | --- | --- | --- |
| | RGR (g·g$^{-1}$·day$^{-1}$) | NAR (mg·dm$^{-2}$·day$^{-1}$) | RGR (g·g$^{-1}$·day$^{-1}$) | NAR (mg·dm$^{-2}$·day$^{-1}$) |
| Non-treated | 0.077 | 53.6 | 0.070 | 40.4 |
| 2 | 0.108 | 77.7 | 0.135 | 61.4 |
| 15 | 0.100 | 75.0 | 0.140 | 60.6 |
| Choline chloride (comparison) | 0.090 | 71.7 | 0.101 | 56.6 |

What is claimed is:

1. A method of promoting the growth of a plant, which comprises applying an effective amount of at least one active compound selected from the group consisting of agriculturally acceptable salts of compounds represented by the formula:

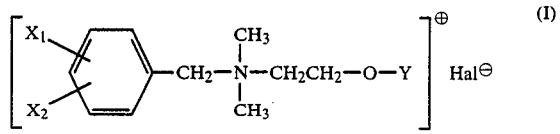

wherein Hal represents a chlorine, bromine or iodine atom, $X_1$ represents a hydrogen or chlorine atom, or a methyl, trifluoromethyl, nitro, methoxy or t-butyl group, and $X_2$ represents a hydrogen atom, or both $X_1$ and $X_2$ represent a chlorine atom or a methyl group; and Y represents a hydrogen atom, or a $C_{2-6}$ alkylcarbonyl, benzoyl, N-phenylcarbamoyl, N-3,4-dichlorophenylcarbamoyl, chloropropylcarbonyl, methoxycarbonyl, carbamoyl or methacryloyl group,
to the stalks, leaves, roots or seeds of the plant or to soil.

2. The method of claim 1 wherein the active compound is applied in the form of an aqueous solution.

3. The method of claim 2 wherein the aqueous solution contains 0.02 to 20% by weight of a surfactant.

4. The method of claim 1 wherein the active compound is applied in the form of an aqueous solution to the stalks and leaves of mature plants at a rate of 3 to 1,500 g per hectare of the cultivated area for the plants.

5. The method of claim 1 wherein seeds of the plants are immersed in an aqueous solution containing the active compound in a concentration of 0.05 to 1,000 ppm.

6. The method of claim 1 wherein an aqueous solution containing the active compound in a concentration of 0.1 to 300 ppm is poured onto parts near the roots of seedlings of the plants.

* * * * *